United States Patent [19]  [11]  4,143,138
Peake et al.  [45]  Mar. 6, 1979

[54] 3-CHLORO-5-(OPTIONALLY SUBSTITUTED HETEROCYCLOXY)-4H-1,2,6-THIADIAZIN-4-ONE ANTIFUNGAL AGENTS

[75] Inventors: Clinton J. Peake; Wayne N. Harnish, both of Medina; Bruce L. Davidson, Middleport, all of N.Y.

[73] Assignee: FMC Corporation, Philadelphia, Pa.

[21] Appl. No.: 904,094

[22] Filed: May 8, 1978

[51] Int. Cl.$^2$ ............... C07D 285/16; A01N 9/12
[52] U.S. Cl. .................................. 424/246; 544/8
[58] Field of Search ........................ 544/8; 424/246

[56] References Cited
U.S. PATENT DOCUMENTS 4,097,594  6/1978  Peake et al. ............. 544/8 X
4,100,281  7/1978  Peake et al. ............. 544/8 X

FOREIGN PATENT DOCUMENTS 854184  5/1977  Belgium.

OTHER PUBLICATIONS

Geevers et al., *Rec. Trav. Chim.*, vol. 93, pp. 270–272 (1974).

*Primary Examiner*—John M. Ford
*Attorney, Agent, or Firm*—Robert L. Andersen; H. Robinson Ertelt

[57] ABSTRACT

Compounds of the formula:

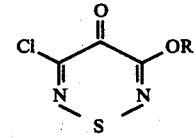

in which R is an optionally substituted heterocyclic ring having 6 members and containing 1 or 2 hetero N atoms, their fungicidal use and preparation are described and exemplified.

4 Claims, No Drawings

3-CHLORO-5-(OPTIONALLY SUBSTITUTED HETEROCYCLOXY)-4H-1,2,6-THIADIAZIN-4-ONE ANTIFUNGAL AGENTS

BACKGROUND OF THE INVENTION

1. Field of the Invention

The present invention relates to novel thiadiazinones which are useful for the control of fungal disease in plants. More particularly the invention relates to 3-chloro-4H-1,2,6-thiadiazin-4-ones which are substituted in the 5-position with selected heterocycloxy groups.

2. Prior Art

Geevers and Trompen described the preparation 3,5-4H-1,2,6-thiadiazin-4-one and its use as an intermediate to prepare various other 3-chloro-4H-1,2,6-thiadiazin-4-ones including, interalia, the 5-chloro and 5-phenoxy derivatives. J. Geevers and W. P. Trompen, *Rec. Trav. Chim.*, 93, 270 (1974). This publication provides no indication of any biological activity for the described compounds. Belgian Pat. No. 854,184, Published Nov. 11, 1977, discloses numerous 5-substituted-3-chloro-4H-1,2,6-thiadiazinones, including inter alia, the 5-(8-quinolinoxy) derivative, and that the disclosed compounds have fungicidal and herbicidal properties.

SUMMARY OF THE INVENTION

In accordance with the present invention there is provided a new group of compounds, 3-chloro-4H-1,2,6-thiadiazin-4-ones substituted at the 5-position with selected heterocycloxy substituents which are hereinafter described, fungicidal compositions of these compounds and a method for providing control of fungal disease in agricultural crops.

DESCRIPTION OF THE INVENTION

The compounds of this invention are 3-chloro-4H-1,2,6-thiadiazin-4-ones having the general formula,

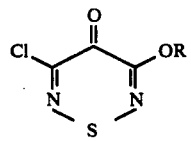

and hydrates thereof, wherein R is an optionally substituted six membered heterocyclic ring consisting of carbon and one or two atoms of nitrogen, one of which may be an N-oxide. Suitable heterocyclic rings include pyridyl, pyridyl-N-oxide, pyrazyl, pyridazyl and pyrimidyl. Preferable compounds are those having the pyridyl or pyridyl-N-oxide heterocyclic ring.

The heterocyclic ring may be unsubstituted or may be substituted with a wide variety of ring substituents. One to three substituents may be employed and may be independently selected from groups such as lower alkyl, halogen, nitro, cyano, lower alkylthio, lower alkylsulfinyl or lower alkylsulfonyl.

Unless otherwise indicated the term "lower" means having 1 to 4 carbon atoms, straight or branched chain and the term halogen means bromine, chlorine, fluorine or iodine.

In the method of this invention an effective fungistatic or fungicidal amount of the above compound as active ingredient is applied to foliage or seeds of agricultural plants or to the soil in which the plants are growing or are to be planted, i.e., the locus where control is desired. When so applied, the compounds prevent fungal infection or inhibit further development of a pre-existing fungal disease.

The selected antifungal agent may be applied as the technical material, or as a formulated product. Typical formulations include the antifungal agent in combination with an agriculturally acceptable carrier, preferably with a surface active agent, and optionally with other active ingredients. Suitable formulations include granules, powders, or liquids, the choice varying with the fungus and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of about 0.5% up to about 99.5% by weight of the formulation. Additives and carriers may comprise about 99.5% by weight to as low as about 0.5% by weight of the formulation. Surface active agents, if employed in the formulation, may be present at various concentrations, suitably in the range of 1% to 30% by weight.

The formulation may be used as such or diluted to a desired use dilution with a suitable diluent or carrier. The concentration of the active ingredient in use dilution is normally in the range of about 0.001% to about 4% by weight. Many variations of spraying, dusting, soil-incorporation may be utilized in applying the compounds. The compounds may be applied as an ingredient of compositions used in the art by substituting or adding a compound of this invention to such compositions.

The antifungal agents of this invention may be formulated and applied with other compatible active ingredients, including nematicides, insecticides, acaricides, other fungicides, plant growth regulators, herbicides, fertilizers, etc.

In applying the foregoing chemicals, whether alone or with other agricultural chemicals, an effective fungistatic or fungicidal amount of the active ingredient must be applied. While the application rate will vary widely depending on the choice of compound, the formulation and mode of application, the plant species being protected, and the planting density, a suitable use rate may be in the range of 0.05 to 5 kg/hectare, preferably 0.5 to about 4 kg/hectare.

The compounds of this invention are prepared by reacting 3,5-dichloro-4H-1,2,6-thiadiazin-4-one with the corresponding heterocyclic alcohol in the presence of a strong base, preferably an amine base such as triethylamine. The following examples are typical of the preparation of the compounds.

EXAMPLE 1

Synthesis of 3,5-Dichloro-4H-1,2,6-thiadiazin-4-one

A 50 ml flask was charged with 20 ml formic acid. The flask was purged with a stream of dry nitrogen. The nitrogen purge was continued while 6.3 g 3,4,4,5-tetrachloro-4H-1,2,6-thiadiazinone was added dropwise over 0.5 hour during which the temperature of the reaction mixture was maintained at 10°±1° C. Following addition the reaction mixture was stirred at 10° C. for 2 hours then at room temperature for 64 hours, then poured into 60 ml. ice-water with stirring. The resulting mixture was filtered and the filter cake washed with water and dried to yield 2.2 g of pale yellow 3,5-dichloro-4H-1,2,6-thiadiazin-4-one, m.p. 81°–82° C.

EXAMPLE 2

Synthesis of 3-chloro-5-(3-pyridyloxy)-4H-1,2,6-thiadiazin-4-one

To a stirred solution of 12.8 grams (0.07 mole) of 3,5-dichloro-4H-1,2,6-thiadiazin-4-one and 6.7 grams (0.07 mole) of 3-hydroxypyridine in 300 ml of tetrahydrofuran was added dropwise 7.1 grams (0.07 mole) of triethylamine. During the addition the exothermic reaction caused the reaction mixture temperature to rise to 34° C. Upon complete addition, the reaction mixture was stirred for 16 hours during which time it cooled to ambient temperature. The reaction mixture was filtered to remove triethylamine hydrochloride. The filter cake was washed with tetrahydrofuran. The filtrate and wash were combined and evaporated under reduced pressure to a residual solid. The residue was triturated with 300 ml of distilled water and the insolubles collected by filtration. The filter cake was washed with water and recrystallized twice from ethanol. A sample of the recrystallized solid was dissolved in chloroform and subjected to analysis by thin layer chromatography. This analysis indicated that the solid contained impurities. The filtrates from the recrystallizations were combined and evaporated under reduced pressure to a residue. The residue was combined with the twice-recrystallized solid and dissolved in chloroform. The solution was slurried with silica gel in an effort to remove the impurities. The mixture was filtered and the filtrate was evaporated under reduced pressure to a residual solid. The solid was recrystallized from ethanol to give 7.0 grams (42%) of 3-chloro-5-(3-pyridyloxy)-4H-1,2,6-thiadiazin-4-one; m.p. 134.5°–135.5° C.

EXAMPLE 3

Synthesis of 3-chloro-5-(6-methyl-3-pyridyloxy)-4H-1,2,6-thiadiazin-4-one

This compound was prepared in the manner of Example 3, using 14.6 grams (0.08 mole) of 3,5-dichloro-4H-1,2,6-thiadiazin-4-one, 8.7 grams (0.08 mole) of 3-hydroxy-6-methylpyridine and 8.9 grams (0.088 mole) of triethylamine in 300 ml of tetrahydrofuran. The crude product was recrystallized from ethanol to give 15.8 grams (77%) of 3-chloro-5-(6-methyl-3-pyridyloxy)-4H-1,2,6-thiadiazin-4-one; m.p. 155°–156° C.

The compounds set forth below are prepared in a manner analogous to that set forth above by substituting an appropriately substituted hydroxy pyridine for that used in Example 3.

| EXAMPLE | COMPOUND | M.P. (° C.) |
|---------|----------|-------------|
| 4 | 3-chloro-5-(2-chloro-3-pyridyloxy)-4H-1,2,6-thiadiazin-4-one | 123.5–124.5 |
| 5 | 3-chloro-5-(1-oxo-3-pyridyloxy)-4H-1,2,6-thiadiazin-4-one hemihydrate | dec. 169 |
| 6 | 3-chloro-5-(2-bromo-3-pyridyloxy)-4H-1,2,6-thiadiazin-4-one | 134–135 |
| 7 | 3-chloro-5-(2-iodo-3-pyridyloxy)-4H-1,2,6-thiadiazin-4-one | 127–128 |
| 8 | 3-chloro-5-(2-nitro-3-pyridyloxy)-4H-1,2,6-thiadiazin-4-one | 142–143 |
| 9 | 3-chloro-5-(5-pyrimidyloxy)-4H-1,2,6-thiadiazin-4-one | |
| 10 | 3-chloro-5-(2-chloro-5-pyrimidyloxy)-4H-1,2,6-thiadiazin-4-one | |

The following examples demonstrate the fungicidal activity of the compounds of this invention. The test organisms used in these examples, together with an identifying code which are in the tables to identify each organism, are as follows:

As = Alternaria solani
Bc = Botrytis cinerea
Cc = Cladosporium cucumerinum
Ep = Erysiphe polygoni
Fs = Fusarium solani
Ho = Helminthosporium oryzae
Pi = Phytophthora infestans
Po = Pyricularia oryzae
Py = Pythium ultimum
Rs = Rhizoctonia solani
Sf = Sclerotinia fructicola
Up = Uromyces phaseoli
Vi = Venturia inaequalis

EXAMPLE 11

Spore Germination Tests

The test chemical was dissolved or suspended in acetone in an amount such that 0.8 ml of the resulting suspension or solution, mixed with 40 ml water agar produced a water agar solution containing 40, 10, 2.5 and 1 ppm of test chemical. The resulting agar solution, at 50° C., was then divided equally between two sterile petri dishes, each having four separated quadrants, and allowed to solidify. Three quadrants of each dish were flooded with 0.1 ml of a spore suspension in sterile water. Spores of two pathogens, *Erysiphe polygoni* and *Uromyes phaseoli*, from infected plant leaves, were brushed on the remaining two quadrants. The tests were then incubated 48 hours, at 24° C.

Readings were then taken and the percentage of germinated spores calculated. From this percentage, a spore germination rating was assigned as follows:

| % Germination | Rating |
|---------------|--------|
| 0–10 | 0 |
| 10–40 | 1 |
| 40–60 | 2 |
| 60–80 | 3 |
| 80–100 | 4 |

Table I reports the inhibitory effect of these test compounds on spore germination. In Table I, the lower the numeral used as a rating, the more effective the compound.

EXAMPLE 12

Mycelial Growth Tests

Aliquots of previously prepared solutions of active ingredient in acetone were added to tubes containing 20 ml of sterile, melted potato dextrose agar that had been cooled to 50° C. to provide mixtures of 40, 20, 10, 5 and 2.5 ppm. The tubes were shaken to ensure thorough mixing of the chemical with the agar, and the mixture poured into petri dishes having 4 quadrants to solidify. Each quadrant was inoculated with a 4 mm diameter disc of agar containing mycelium of the test fungi and incubated at 25° C. for 72 to 144 hours, depending on the species being employed, during which the samples were alternately exposed to light for 12 hours and to darkness for 12 hours. Growth was measured at the end of the incubation period by measuring the diameter of each fungus colony. Two measurements of the diameter, perpendicular to each other, were taken and the values averaged. Data are reported as percent inhibition (%I) by the following formula:

$$\%I = \frac{\text{mm growth of check} - \text{mm growth of treated sample}}{\text{mm growth of check}} \times 100$$

The results reported in Table II indicate a high level of activity for the test compounds.

TABLE I

SPORE GERMINATION INHIBITION TESTING

| Compound of Example | Conc.a.i. ppm | Spore Germination Rating | | | | | | | |
|---|---|---|---|---|---|---|---|---|---|
| | | Bc | Po | Vi | As | Cc | Pi | Ep | Up |
| 2 | 40 | 0 | 0 | 0 | 0 | 0 | 0 | 0 | 0 |
|   | 10 | 0 | 0 | 0 | 0 | 0 | 0 | 0 | 0 |
|   | 2.5 | 0 | 0 | 0 | 0 | 0 | 0 | 0 | 0 |
|   | 1.0 | 4 | 2 | 0 | 0 | 0 | 0 | 1 | 0 |
| 3 | 40 | 0 | 0 | 0 | 0 | 0 | 0 | 0 | 0 |
|   | 10 | 0 | 0 | 0 | 0 | 3 | 0 | 4 | 2 |
|   | 2.5 | 0 | 0 | 0 | 0 | 3 | 0 | 4 | 2 |
|   | 1.0 | 4 | 1 | 0 | 0 | 4 | 0 | 4 | 2 |
| 4 | 40 | 0 | 0 | 0 | 0 | 0 | 0 | 0 | 0 |
|   | 10 | 0 | 0 | 0 | 0 | 0 | 0 | 0 | 0 |
|   | 2.5 | 0 | 0 | 0 | 0 | 0 | 0 | 0 | 0 |
|   | 10 | 2 | 0 | 0 | 3 | 0 | 0 | 0 | 0 |
| 5 | 40 | 4 | 0 | 0 | 0 | 0 | 0 | 0 | 0 |
|   | 10 | 4 | 3 | 2 | 4 | 4 | 0 | 0 | 0 |
|   | 2.5 | 4 | 4 | 4 | 4 | 4 | 3 | 2 | 4 |
|   | 1.0 | 4 | 4 | 4 | 4 | 4 | 4 | 4 | 4 |
| 6 | 40 | 0 | 0 | 0 | 0 | 0 | 0 | 0 | 0 |
|   | 10 | 0 | 0 | 0 | 0 | 0 | 0 | 0 | 0 |
|   | 2.5 | 0 | 0 | 0 | 0 | 0 | 0 | 0 | 0 |
| 7 | 40 | 0 | 0 | 0 | 0 | 0 | 0 | 2 | 0 |
|   | 10 | 0 | 0 | 0 | 0 | 0 | 0 | 4 | 0 |
|   | 2.5 | 0 | 0 | 1 | 4 | 0 | 0 | 0 | 0 |
| 8 | 40 | 0 | 0 | 0 | 0 | 0 | 0 | 0 | 0 |
|   | 10 | 0 | 0 | 0 | 0 | 0 | 0 | 2 | 0 |
|   | 2.5 | 0 | 0 | 2 | 4 | 0 | 0 | 3 | 0 |

TABLE II

IN VITRO MYCELIAL GROWTH INHIBITION EVALUATIONS

| Compound of Example | Conc.a.i. ppm | Percent Fungus Growth Inhibition | | | | | | | |
|---|---|---|---|---|---|---|---|---|---|
| | | As | Fs | Sf | Po | Py | Rs | Ho | Cc |
| 2 | 40 | 100 | 100 | 100 | 100 | 100 | 96 | 100 | 100 |
|   | 20 | 100 | 100 | 100 | 58 | 100 | 100 | 100 | 100 |
|   | 10 | 100 | 100 | 100 | 29 | 100 | 56 | 100 | 62 |
|   | 5 | 100 | 63 | 48 | 33 | 100 | 31 | 100 | 38 |
| 3 | 40 | 100 | 100 | 100 | 9 | 100 | 100 | 100 | 71 |
|   | 20 | 100 | 100 | 94 | 0 | 100 | 64 | 100 | 100 |
|   | 10 | 100 | 100 | 82 | 0 | 100 | 64 | 100 | 100 |
|   | 5 | 100 | 56 | 74 | 9 | 47 | 31 | 100 | 100 |
| 4 | 40 | 100 | 100 | 100 | 100 | 100 | 69 | 100 | 100 |
|   | 20 | 100 | 100 | 100 | 100 | 100 | 56 | 100 | 62 |
|   | 10 | 47 | 100 | 81 | 65 | 100 | 42 | 100 | 45 |
|   | 5 | 47 | 100 | 48 | 52 | 69 | 39 | 100 | 31 |
| 5 | 40 | 67 | 100 | 57 | 91 | 100 | 69 | 100 | 52 |
|   | 20 | 31 | 75 | 25 | 64 | 100 | 20 | 100 | 31 |
|   | 10 | 13 | 58 | 0 | 32 | 76 | 11 | 100 | 10 |
|   | 5 | 0 | 17 | 0 | 27 | 0 | 0 | 7 | 10 |
| 6 | 10 | 100 | 100 | 87 | 90 | 100 | 64 | 100 | 56 |
|   | 5 | 100 | 43 | 61 | 90 | 100 | 53 | 64 | 35 |
|   | 2.5 | 71 | 21 | 55 | 42 | 7 | 20 | 64 | 19 |
| 7 | 10 | 100 | 100 | 100 | 81 | 100 | 64 | 100 | 68 |
|   | 5 | 100 | 29 | 74 | 48 | 45 | 42 | 50 | 34 |
|   | 2.5 | 62 | 57 | 61 | 43 | 53 | 42 | 45 | 25 |
| 8 | 10 | 90 | 86 | 100 | 100 | 100 | 78 | 100 | 100 |
|   | 5 | 90 | 64 | 74 | 52 | 87 | 53 | 75 | 72 |
|   | 2.5 | 62 | 21 | 55 | 24 | 33 | 53 | 55 | 38 |

What is claimed is:

1. A compound of the formula

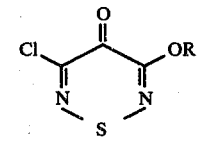

and hydrates thereof, wherein R is a six membered heterocyclic ring consisting of carbon and one or two atoms of nitrogen, one of which may be an N-oxide, optionally substituted with one to three substituents independently selected from lower alkyl, halogen, nitro, cyano, lower-alkylthio, lower alkylsulfinyl and lower alkylsulfonyl.

2. A fungicidal composition comprising a fungistatic or fungicidal amount of the compound of claim 1 in admixture with an agriculturally acceptable carrier.

3. A method of controlling fungal damage to agricultural crops which comprises applying to the locus of infestation a fungistatic or fungicidal amount of the compound of claim 1.

4. The compound of claim 1 wherein said heterocyclic ring is optionally substituted pyridyl or pyridyl-N-oxide and agriculturally acceptable hydrates thereof.

* * * * *

UNITED STATES PATENT AND TRADEMARK OFFICE
CERTIFICATE OF CORRECTION

PATENT NO. : 4,143,138
DATED : March 6, 1979
INVENTOR(S) : Clinton J. Peake, et al.

It is certified that error appears in the above-identified patent and that said Letters Patent are hereby corrected as shown below:

Column 5, line 12, "%I =" should read $$\%I = \frac{mm \text{ growth of check} - mm \text{ growth of treated sample}}{mm \text{ growth of check}} \times 100$$

Column 5, Table I, Compound of Example 4 should read

TABLE I

SPORE GERMINATION INHIBITION TESTING

| Compound of Example | Conc. a.i. ppm | Spore Germination Rating | | | | | | | |
|---|---|---|---|---|---|---|---|---|---|
| | | Bc | Po | Vi | As | Cc | Pi | Ep | Up |
| 4 | 40 | 0 | 0 | 0 | 0 | 0 | 0 | 0 | 0 |
| | 10 | 0 | 0 | 0 | 0 | 0 | 0 | 0 | 0 |
| | 2.5 | 0 | 0 | 0 | 0 | 0 | 0 | 0 | 0 |
| | 1.0 | 2 | 0 | 0 | 3 | 0 | 0 | 0 | 0 |

UNITED STATES PATENT AND TRADEMARK OFFICE
CERTIFICATE OF CORRECTION

PATENT NO. : 4,143,138
DATED : March 6, 1979
INVENTOR(S) : Clinton J. Peake, et al.

It is certified that error appears in the above-identified patent and that said Letters Patent are hereby corrected as shown below:

Column 6, Table II, Compound of Example 7 should read

TABLE II
IN VITRO MYCELIAL GROWTH INHIBITION EVALUATIONS

Percent Fungus Growth Inhibition

| Compound of Example | Conc.a.i. ppm | As | Fs | Sf | Po | Py | Rs | Ho | Cc |
|---|---|---|---|---|---|---|---|---|---|
| 7 | 10 | 100 | 100 | 100 | 81 | 100 | 64 | 100 | 68 |
|   | 5 | 100 | 29 | 74 | 48 | 45 | 42 | 50 | 34 |
|   | 2.5 | 62 | 57 | 61 | 43 | 53 | 42 | 55 | 25 |

Signed and Sealed this

Twenty-fifth Day of September 1979

[SEAL]

Attest:

LUTRELLE F. PARKER

*Attesting Officer*  *Acting Commissioner of Patents and Trademarks*